(12) United States Patent
Mande et al.

(10) Patent No.: US 9,116,839 B2
(45) Date of Patent: Aug. 25, 2015

(54) PREDICTION OF HORIZONTALLY TRANSFERRED GENE

(75) Inventors: Sharmila Shekhar Mande, Hyderabad (IN); Varun Mehra, Andhra Pradesh (IN); Tarini Shankar Ghosh, Andhra Pradesh (IN)

(73) Assignee: Tata Consultancy Services Limited (IN)

(*) Notice: Subject to any disclaimer, the term of this patent is extended or adjusted under 35 U.S.C. 154(b) by 519 days.

(21) Appl. No.: 13/472,737

(22) Filed: May 16, 2012

(65) Prior Publication Data

US 2013/0226465 A1 Aug. 29, 2013

(30) Foreign Application Priority Data

Feb. 24, 2012 (IN) .......................... 504/MUM/2012

(51) Int. Cl.
*G06F 19/14* (2011.01)
*G06F 19/24* (2011.01)
*G06K 9/62* (2006.01)

(52) U.S. Cl.
CPC ................ *G06F 19/14* (2013.01); *G06F 19/24* (2013.01); *G06K 9/622* (2013.01); *G06K 9/6268* (2013.01)

(58) Field of Classification Search
CPC ................................ G06F 19/22; G06F 19/14
See application file for complete search history.

(56) References Cited

U.S. PATENT DOCUMENTS

| | | | |
|---|---|---|---|
| 6,900,015 B2 | 5/2005 | Avihingsanon et al. | |
| 2002/0183644 A1* | 12/2002 | Levendowski et al. | 600/544 |
| 2004/0107221 A1* | 6/2004 | Trepess et al. | 707/104.1 |
| 2005/0207630 A1* | 9/2005 | Chan et al. | 382/131 |
| 2005/0267692 A1* | 12/2005 | Tsirigos et al. | 702/20 |

OTHER PUBLICATIONS

Liao, W., Liu, Y. & Choudhary, A. A Grid-based Clustering Algorithm using Adaptive Mesh Refinement. in Seventh Work. Min. Sci. Eng. Datasets conjunction with SIAM Int. Conf. Data Min. (2004).*
Sandberg, R. et al. Capturing whole-genome characteristics in short sequences using a naïve Bayesian classifier. Genome Res. 11, 1404-1409 (2001).*
Dasgupta, S. Experiments with random projection. in Conference on Uncertainty in Artificial Intelligence (Boutilier, C. & Goldszmidt, M.) 143-151 (Morgan Kaufmann Publishers Inc., 2000).*
Kaski, S. Dimensionality reduction by random mapping: fast similarity computation for clustering. in IEEE International Joint Conference on Neural Networks 1, 413-418 (IEEE, 1998).*

(Continued)

*Primary Examiner* — Soren Harward
(74) *Attorney, Agent, or Firm* — Schwegman Lundberg & Woessner, P.A.

(57) ABSTRACT

Method(s) and system(s) for identifying horizontally transferred genes are described herein. The method includes defining a cuboid in a three dimensional space, wherein the cuboid includes fragment points corresponding to the genomic fragments belonging to a plurality of sequenced microbial genomes, and dividing the cuboid into a plurality of grids. The method further includes selecting one or more grids corresponding to a selected genome and classifying each of the selected grids as one of majority, minority, and mixed grids, based on number of fragment points corresponding to the selected genome in each of the selected grids. Further, at least one genomic fragment from the minority and the mixed grids is identified as the horizontally transferred gene based on a distance ratio assessment.

16 Claims, 8 Drawing Sheets

(56) References Cited

OTHER PUBLICATIONS

Azad, Rajeev K., et al., "Towards more robust methods of alien gene detection", Nucleic Acids Research, 2011, vol. 39, No. 9, (Feb. 4, 2011), 11 pgs.

Ghosh, Tarini Shankar, et al., "HabiSign: a novel approach for comparison of metagenomes and rapid identification of habitatspecific sequences", BMC Bioinformatics 2011, 12(Suppl 13):S9, (Dec. 2, 2011), 11 pgs.

Rajan, Issaac, et al., "Identification of compositionally distinct regions in genomes using the centroid method", Bioinformatics Oxford Journals, vol. 23, No. 20 2007, (Aug. 27, 2007), 2672-2677.

Shrivastava, Sakshi, et al., "INDeGenIUS, a new method for high-throughput identification of specialized functional islands in completely sequenced organisms", J. Biosci. 35(3), Sep. 2010, Indian Academy of Sciences, (Sep. 2010), 351-364.

* cited by examiner

PREDICTION OF HORIZONTALLY TRANSFERRED GENE

CLAIM OF PRIORITY

This application claims the benefit of priority under 35 U.S.C. §119 of Sharmila Shekhar Mande, Indian Patent Application Serial Number 504/MUM/2012, entitled "PREDICTION OF HORIZONTALLY TRANSFERRED GENE," filed on Feb. 24, 2012, the benefit of priority of which is claimed hereby, and which is incorporated by reference herein in its entirety.

The present subject matter relates, in general, to the field of genomics and, in particular, to prediction of horizontally transferred genes.

BACKGROUND

Genomics is a field of active research today. Genetic material obtained from an organism is generally sequenced into a plurality of sequences, called genomic sequences. The genomic sequences may be further analyzed to study the characteristics of the corresponding genome, for example, to identify genes and to study the interaction between the genes constituting the genomic sequences. For obtaining a holistic view of the functioning and survival strategies of a given organism in its associated environment, there is not only a need to study each of the individual genomes in isolation, but also a need to understand the extent and the mode of exchange of genomic information across the genomes of diverse organisms in its environment.

A comparative analysis of the genomes of diverse organisms in the same environmental sample has revealed the presence of genes or gene clusters that show a pattern of inheritance that is different from the established phylogenetic tree of life. These genes or gene clusters show a higher sequence homology to genes originating from organisms belonging to different taxonomic clades, than to its close phylogenetic relatives. These genes or gene clusters are observed to be shared across organisms which inhabit the same micro-environment (i.e. physical proximity) rather than the phylogenetic closeness between these organisms. Such physical proximity of different organisms within the same micro-environment increases the chances of exchange of genetic material across diverse species.

The process of exchanging genomic material as a result of which an organism incorporates part of the genetic material from another organism is known as horizontal gene transfer or lateral gene transfer. Such gene-transfer events allow large regions of foreign DNA (Deoxyribonucleic Acid) from 'donor' genome to be inserted into the native 'recipient' genome and are generally observed to have an oligonucleotide usage pattern distinct from that of the native recipient genome. These exchanged genes or gene-clusters are referred to as horizontally transferred genes or HGT regions.

The horizontally transferred genes confer a selective advantage to the organisms in terms of their growth and survival in the given environment. For instance, such genes or gene-clusters may confer various characteristics, such as resistance against multitude of antibiotics (for example, multidrug resistance gene operons), virulence associated functions comprising secretion machineries (for example, Type III, Type IV, Type VI secretion machineries), and specialized machineries providing defense mechanisms against host immune response in pathogenic organisms. These also include genes that facilitate chemotaxis and adhesion of recipient bacteria to host cell membranes and even those encoding specialized metabolic enzymes that increase the survival chances of the recipient organisms in nutrient-deficient environments.

Thus, efficient detection of such HGT regions in genomes of different organisms provide useful insights in understanding the probable mechanisms of transfer of such genes and in identifying the specific functions that enhance the survival of the recipient organisms in diverse micro-environments.

SUMMARY

This summary is provided to introduce concepts related to prediction of horizontally transferred genes, and the concepts are further described below in the detailed description. This summary is not intended to identify essential features of the claimed subject matter nor is it intended for use in determining or limiting the scope of the claimed subject matter.

Method(s) and system(s) for prediction of horizontally transferred gene are described. A plurality of genomic fragments, obtained by splitting a plurality of genomes of completely sequenced microbial organisms, are transformed into fragment points in a three dimensional space. A cuboid is defined in the three dimensional space such that the cuboid includes the fragment points corresponding to all the genomic fragments. The cuboid is further divided into a plurality of smaller equally sized cuboids referred to as grids. The fragment points falling into one grid are grouped together and a centroid is computed for each grid. One or more grids having the fragment points corresponding to a particular genome are selected and each of the selected grids is classified as one of majority, minority, and mixed grids with respect to the particular genome. Further, one or more of the genomic fragments are identified as horizontally transferred genes from the minority and mixed grids based on a distance ratio assessment.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Figure 1A:
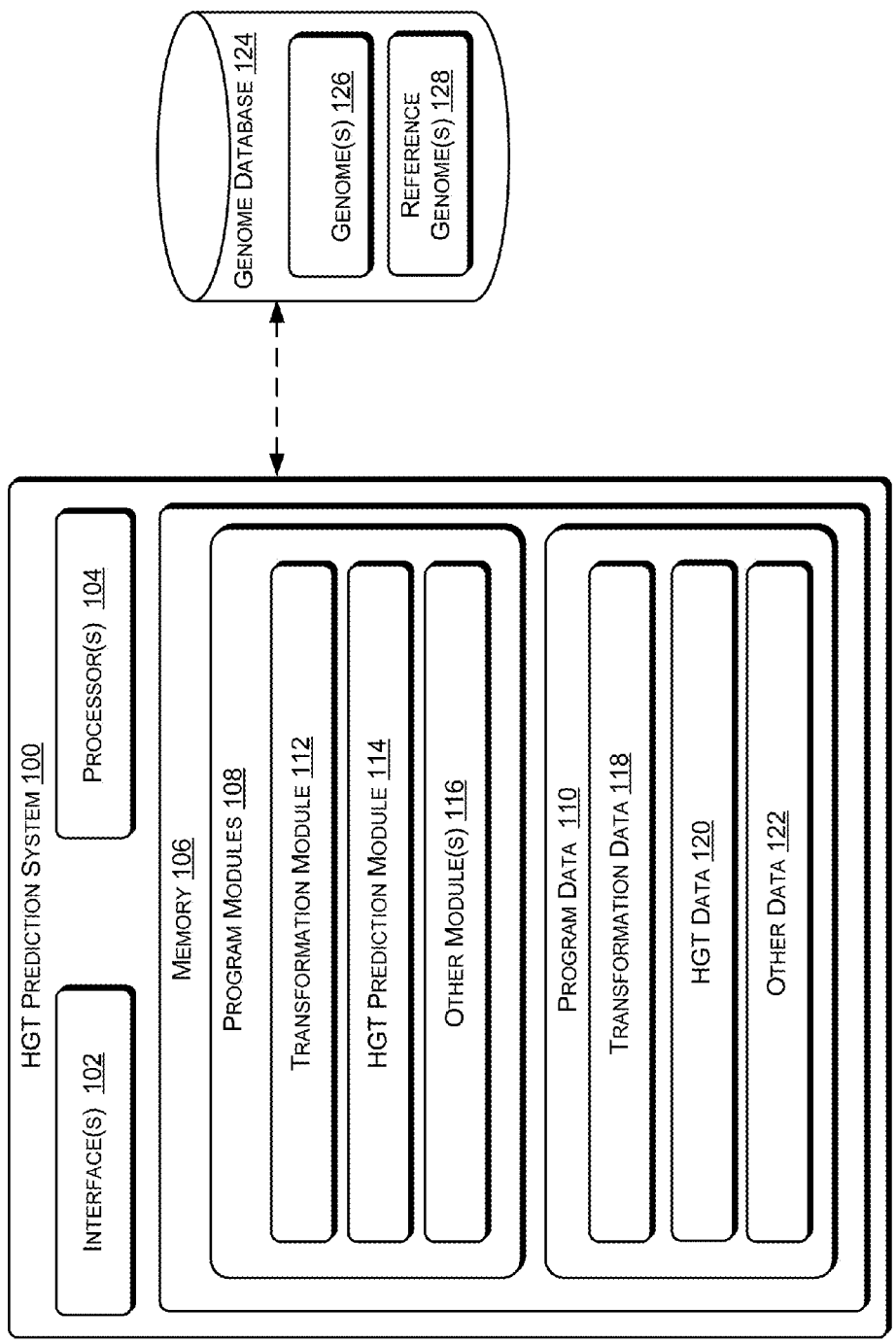
FIG. 1(a) illustrates an exemplary system for horizontally transferred gene prediction, in accordance with an embodiment of the present subject matter.

Genetic material extracted from an organism is sequenced into a plurality of genomic sequences, assembled as complete genomes and further stored as genomic data in reference databases for research and medical purposes. Further, as discussed earlier, various phylogenetic studies are carried out to identify the horizontally transferred genes across microbial organisms. As will be understood, the horizontally transferred genes refer to genes transferred from one organism to another organism. Such genes can cause significant changes in characteristics of the organism receiving the genes.

Typically, similarity-based approaches have been followed to identify the horizontally transferred genes. However, the similarity-based approaches are limited by the presence or absence of homologous or orthologous genes in the existing databases of genome, thus affecting the efficiency of identifying the horizontally transferred genes. Another approach involves using parametric measures, such as percentage of Cytosine and Guanine (C+G) % content and di-nucleotide frequency differences ($\delta^*$) either in isolation or in combination, to identify horizontally transferred genes. Determining the parametric measures facilitates in identifying horizontally transferred genes within a given microbial genome. However, most of the parametrical measures detect similar probable HGT regions and therefore, using these parametric measures simultaneously may result in overlapping peaks rather than better detection of HGT regions.

Further, some conventional methods use frequencies of higher oligonucteotides, such as octamer frequencies, to achieve better sensitivities with lower false positive rate. Sensitivity may be defined as a percentage of compositionally distinct regions correctly identified as horizontally transferred genes. False positive rate may be computed as specificity subtracted from 100, where specificity is the percentage of non-HGT regions correctly identified as non-HGT by any method. Thus, the false positive rate is an indicator of likelihood of wrongly identifying a non-HGT region as an HGT region.

Most of the existing horizontally transferred gene prediction methods identify only those genomic regions as HGT, which have oligonucieotide compositions statistically different from that of its native genome. These methods generally scan the whole genomes with large window sizes of 5-10 kilo base pairs. Using such methods may result in missing out the subtle variations in oligonucleotide usage patterns of genes observed for smaller regions within such large windows. The subtle variations in oligonucletides usage patterns may highlight the amelioration occurring over the course of evolution for those genes corresponding to these smaller regions.

Additionally, most of the above approaches are based on determination of the compositionally distinct or atypical region of an organism's genome in comparison to its whole native genome, based on averaging the value of a given parametric measure across the whole genome. The average value is subsequently compared against a value obtained for a genomic fragment window in consideration. However, in this approach of averaging out the values across the whole genome, liner variations in oligonucleotide usage patterns may remain undetected.

In accordance with the present subject matter, method(s) and system(s) for prediction of horizontally transferred genes are described. The methods and the systems facilitate identification of horizontally transferred genes or cluster of genes. In one embodiment, genomic data of a plurality of genomes is retrieved from a genome database. In one implementation, the plurality of genomes is split into a plurality of base pair fragments, hereinafter referred to as genomic fragments. For example, the plurality of genomes may be split into 1000 base pair fragments. Each of the genomic fragments is subsequently transformed to a fragment point in the three dimensional space using, for example, a set of reference points obtained from a plurality of reference genomes.

Further, in one implementation, a cuboid may be defined in the three dimensional space such that the cuboid encloses all the fragment points. Further, the cuboid may be divided into a plurality of smaller equally sized cuboids called grids, such that each grid includes the fragment points located in the coordinates defined by the particular grid. Thus, some of the grids may include no fragment points, while other grids may include one or more fragment points. The plurality of grids may then be analyzed to identify dense grids, i.e., grids in which the number of fragment points corresponding to genomic fragments is greater than a predefined percentage of the fragments point corresponding to the genomic fragments initially obtained. The dense grids are further resolved into smaller grids with a new set of reference points obtained from the plurality of reference points. This process of identifying dense grids and further resolving them into smaller grids may be continued until there are no further dense grids to be resolved based on the predefined threshold. A centroid corresponding to each of the grids finally obtained is identified and stored.

Each of the grids thus obtained is further analyzed and classified as one of minority, majority, and mixed grids for a selected genome. In one implementation, the classification is based on a plurality of threshold values determined from quartile values computed on the basis of a quantile function value approach. Based on the classification, the minority and the mixed grids are further analyzed for identification of horizontally transferred genes.

In one embodiment, a distance ratio assessment may be performed for determining probable horizontally transferred genes from among the genomic fragments, fragment points corresponding to which are present in the mixed grids and the minority grids. The grid in which the fragment point of the genomic fragment lies is referred to as home grid and grids immediately adjacent to the home grid are referred to as neighboring grids. The distance ratio assessment, in one embodiment, includes computation of the ratio of the distance of a fragment point from the centroid of a home grid to the distance of the centroid of the home grid from the centroid of a neighboring grid, referred to as distance ratio. Based on the distance ratio assessment, the fragment points having a distance ratio of less than a distance threshold, for example, 0.5, for all neighboring grids may correspond to probable horizontally transferred genes. On the other hand, the fragment points having a distance ratio of more than or equal to 0.5 for one or more neighboring grids may be attached to the nearest neighboring grid and subsequently analyzed for prediction as a probable horizontally transferred gene following the complete work-flow described above for that neighboring grid. The grid-by-grid assessment of genomic fragments is continued until the minority and mixed grids of the selected genome have been assessed. Additionally, a confidence value may be attached to the predicted horizontally transferred genes. The confidence value represents the confidence with which a predicted horizontally transferred gene can be said to be an actual horizontally transferred gene.

The present subject matter thus enables identification of horizontally transferred genes with higher sensitivity. Further, since the present method uses genomic fragments of relatively smaller length, such as 1 kilo base pair (Kb), subtle variations in oligonucleotide composition within the HGT region across the given microbial genome can also be identified with higher efficiency. The present subject matter also ensures that the mapping of one region of genome is independent of another region of the same genome, therefore resulting in efficient detection of the subtle variations. Further, the compositionally distinct or atypical regions, referred to as HGT, of any microbial genome are identified by taking the oligonucleotide usage patterns corresponding to genomic fragments belonging to all known microbial genomes into consideration in a single framework. Thus, overall sensitivity that can be achieved is higher as compared to conventional methods of HGT prediction.

These and other advantages of the present subject matter would be described in greater detail in conjunction with the following figures. While aspects of described systems and methods for horizontally transferred gene prediction can be implemented in any number of different computing systems environments, and/or configurations, the embodiments are described in the context of the following system(s).

The manner in which the horizontally transferred genes (hereinafter referred to as HGT) are identified shall be explained in detail with respect to the figures. While aspects of prediction of HGT can be implemented in any number of different computing systems environments, and/or configurations, the embodiments are described in the context of the following exemplary system architecture(s). It would be appreciated that other implementations are also covered without deviating from the scope of the present subject matter.

FIG. 1(a) illustrates an exemplary HGT prediction system 100, according to an implementation of the present subject matter. The HGT prediction system 100 can be implemented in systems that include, but are not limited to, desktop computers, hand-held devices, multiprocessor systems, personal digital assistants (PDAs), laptops, network computers, cloud servers, minicomputers, mainframe computers, and the like. In one implementation, the HGT prediction system 100 includes interface(s) 102, one or more processor(s) 104, and a memory 106 coupled to the processor(s) 104.

The interfaces 102 may include a variety of software and hardware interfaces, for example, internees for peripheral device(s), such as a keyboard, a mouse, an external memory, and a printer. Further, the interfaces 102 may enable the HGT prediction system 100 to communicate with other computing systems, such as web servers and external databases. The interfaces 102 can facilitate multiple communications within a wide variety of networks and protocol types, including wired networks, for example, local area network (LAN), cable, etc., and wireless networks, such as, Wireless LAN (WLAN), cellular, or satellite. For the purpose, the interfaces 102 may include one or more ports for connecting a number of computing systems with one another or to another server computer.

The processor 104 can be a single processing unit or a number of units, all of which could include multiple computing units. The processor 104 may be implemented as one or more microprocessors, microcomputers, microcontrollers, digital signal processors, central processing units, state machines, logic circuitries, and/or any devices that manipulate signals based on operational instructions. Among other capabilities, the processor 104 is configured to fetch and execute computer-readable instructions and data stored in the memory 106.

The memory 106 may include any computer-readable medium known in the art including, for example, volatile memory such as static random access memory (SRAM) and dynamic random access memory (DRAM), and/or non-volatile memory, such as read only memory (ROM), erasable programmable ROM, flash memories, hard disks, optical disks, and magnetic tapes. The memory 106 also includes program module(s) 108 and program data 110.

The program modules 108, amongst other things, include routines, programs, objects, components, data structures, etc., which perform particular tasks or implement particular abstract data types. The program modules 108 further include, for example, a transformation module 112, an HGT prediction module 114, and other module(s) 116. The other modules 116 may include programs that supplement applications on the HGT prediction system 100, for example, programs in the operating system. On the other hand, the program data 110 serves, amongst other things, as a repository for storing data processed, received, and generated by one or more of the program modules 108. The program data 110 includes, for example, transformation data 118, HGT data 120, and other data 122. The other data 122 includes data generated as a result of the execution of one or more modules in the other modules 116.

In one implementation, the HGT prediction system 100 is associated with a genome database 124. The genome database 124 can be either external or internal to the HGT prediction system 100. The genome database 124 includes genome sequences corresponding to a plurality of genomes 126 and a plurality of reference genomes 128. The plurality of genomes 126 correspond to genomes of completely sequenced microbial organisms. The reference genome(s) 128 includes one representative genome from each of the known genera.

In one implementation, the transformation module 112 retrieves the plurality of genomes 126 of completely sequenced microbial organisms from the genome database 124. For example, the genomes 126 may correspond to 1005 genomes of completely sequenced microbial organisms as available in the National Center for Biotechnology Information (NCBI) public database. The transformation module 112 splits the plurality of genomes 126 into a plurality of base pair fragments (hereinafter referred to as genomic fragments). For example, each of the 1005 genomes can be split into 1000 base pair genomic fragments. Further, the transformation module 112 transforms each genomic fragment into a point in a three dimensional space, referred to as fragment point. For transforming a particular genomic fragment, the transformation module 112 obtains the frequencies of all possible tetranucleotides in the given sequence corresponding to the particular genomic fragment and represents the particular genomic fragment as a 256 dimensional vector. The obtained 256 dimensional vector is further transformed to a three dimensional vector corresponding to x, y, and z coordinates by computing the distance between the 256 dimensional vector and a set of three reference points. The set of reference points are chosen so that they not only represent the tetranucleotide usage patterns observed in the known biological realm, but are also most distinct among each other.

In one implementation, for determining the set of reference points, the transformation module 112 retrieves the plurality of reference genomes 128 from the genome database 124. Each genome from the reference genomes 128 may be representative of a different genus. For example, 237 completely sequenced microbial genomes may be retrieved from the genome database 124. The transformation module 112 splits the plurality of reference genomes into a plurality of non-overlapping reference genomic fragments. For example, each of the 237 reference genomes may be split into 1000 base pair non-overlapping reference genomic fragments reined to as reference fragments. Further, a fragment vector containing the frequencies of all possible 256 tetra-nucleotides is computed for each reference fragment. The transformation module 112 then clusters the fragment vectors by using a clustering approach. In one implementation, K-means approach may be used for clustering of the fragment vectors using Manhattan distance between individual vectors as the similarity criterion. The number of clusters to be generated may be computed by any method known in the art, for example, using equation (1).

$$k \approx \sqrt{\frac{n}{2}} \quad (1)$$

In equation (1), k is total number of clusters to be obtained and N is total number of reference genomic fragments obtained from the reference genomes 128. For example, 631 clusters may be created from 237 reference genomes mentioned in the above example. Further, the transformation module 112 computes cluster vectors corresponding to centroid of each cluster and obtains pairwise dot products of the unit cluster vectors. Subsequently, the three cluster vectors having the least pairwise dot product amongst them are selected as the set of reference points.

The transformation module 112 uses the obtained set of reference points to transform the 256 dimensional vectors of the genomic fragments obtained from the genomes 126 into the fragment points in the three dimensional space. For this, the transformation module 112 computes the distance between the 256 dimensional vectors and the set of three reference points to obtain the three dimensional vectors corresponding to x, y, and z coordinates of the fragment points.

The fragment points thus obtained are then grouped into bins, called as grids, by the HGT prediction module 114. For this, the HGT prediction module 114 first defines a cuboid in the three dimensional space. The range of the cuboid in each of the x, y and z directions is determined as the difference of maximum and minimum value for each of the x, y, and z coordinates of the fragment points. The cuboid thus formed contains the fragment points corresponding to all the genomic fragments obtained from the genomes 126, and is also referred to as the first cuboid. For example, the HGT prediction module 114 may obtain 100,000 genomic fragments initially and transform each of the 100,000 genomic fragments into a plurality of fragment points in the three dimensional space using the first set of reference points. Then, the HGT prediction module 114 defines a cuboid in the three dimensional space containing fragment points corresponding to the 100,000 genomic fragments.

The HGT prediction module 114 divides the first cuboid into a set of smaller equally sized cuboids called grids. The HGT prediction module 114 groups together all the fragments falling into one grid and identifies the number of the fragment points corresponding to genomic fragments falling into each grid. If the number of fragment points in a grid is equal to or more than a predefined percentage of the total number of the genomic fragments being analyzed, such grids are referred to as dense grids. Referring to the above example, the HGT prediction module 114 divides the first cuboid into a first set of 1000 equal grids. In one implementation, the 100,000 fragment points may be localized in about 300 grids leaving the remaining 700 grids void. Out of these 300 occupied grids, 50 grids may have fragment points above a predefined percentage, say 5% of total number of initial 100,000 fragments points. In the given example, 50 grids are found to contain more than 5000 fragment points in them and thus are described as dense grids.

The HGT prediction module 114 resolves the dense grids into a second set of grids using a second set of reference points. The second set of reference points may correspond to the three cluster vectors having the next least pairwise dot products (i.e. least $4^{th}$, $5^{th}$, and $6^{th}$ pair dot product) amongst them.

To resolve a dense grid using the second set of reference points, the distances of the fragment points in the dense grid are determined from the second set of reference points to obtain a second set of fragment points with new x, y, and z coordinates. A second cuboid is formed from the second set of fragment points corresponding to the genomic fragments in the dense grid. The HGT prediction module 114 divides the second cuboid into a second set of equal grids from which dense grids are again identified in the same manner as discussed above for the first cuboid. The second round of resolving the dense grids having fragment points above a pre-defined threshold results in efficient partitioning of the large number of compositionally similar fragment points localized in few grids, 50 grids in this example.

The whole process of resolving the dense grids is further repeated until the number of the fragment points corresponding to the genomic fragments in all grids is less than the predefined percentage of the total number of genomic fragments. For instance, five grids from the previous example may stilt contain fragment points above the predefined percentage, i.e., 5% of the total number of fragment points. This is due to a very high localization of fragment points in these five grids. Thus, in order to efficiently resolve these highly dense grids for further efficient partitioning of large number of compositionally similar fragments points localized in these grids, a third round of resolving is performed. The HGT prediction module 114 resolves these highly dense grids into a third set of grids, for example, 11000 equal grids in each of the five grids, using a third set of reference points. The third set of reference points may correspond to the three cluster vectors having the next least pairwise dot products, i.e., least $7^{th}, 8^{th}$ and $9^{th}$ pairwise dot product, amongst them. This third round of resolving these few highly dense grids still having fragment points above a pre-defined threshold results in highly efficient partitioning of the large number of compositionally similar fragment points localized in these grids, five grids in this example. The HGT prediction module 114 keeps on resolving the dense grids till there are no further grids having number of fragment points corresponding to the genomic fragments above the predefined percentage, 5% in this example, of the total number of fragments, 100,000 genomic fragments in this example. Further, the process of resolving dense grids will be explained in detail with reference to FIG. 4.

Further, the HGT prediction module 114 computes a centroid for each of the grids thus obtained. In one implementation, equation (2) may be used for computing the centroid corresponding to each grid $$r = (1/n) * (\Sigma r_k) \quad (2)$$

Where, $r_k = k^{th}$ position vector in the space and r is the centroid for points $r_k$, where $k \in [0, n]$ The grids thus determined have the all the fragment points corresponding to the plurality of genomic fragments belonging to the plurality of genomes 126. The genome for which the horizontally transferred genes or HGT are to be detected is first selected, for example, by a user using the HGT prediction system 100. The grids are then analyzed to determine the number of fragment points corresponding to the genomic fragments of each genome in each grid. The grid having a majority of fragment points corresponding to the genomic fragments of the selected genome in comparison to the fragment points corresponding to the genomic fragments of other genomes is referred to as majority grid for the selected genome. Similarly, if the number of fragment points corresponding to the genomic fragments of the selected genome is in minority, the grid is referred as a minority grid for the selected genome. If the number of fragment points corresponding to the genomic fragments of the selected genome is neither in majority nor in minority, the grid is referred to as a mixed grid with respect to that genome.

Figure 1B:
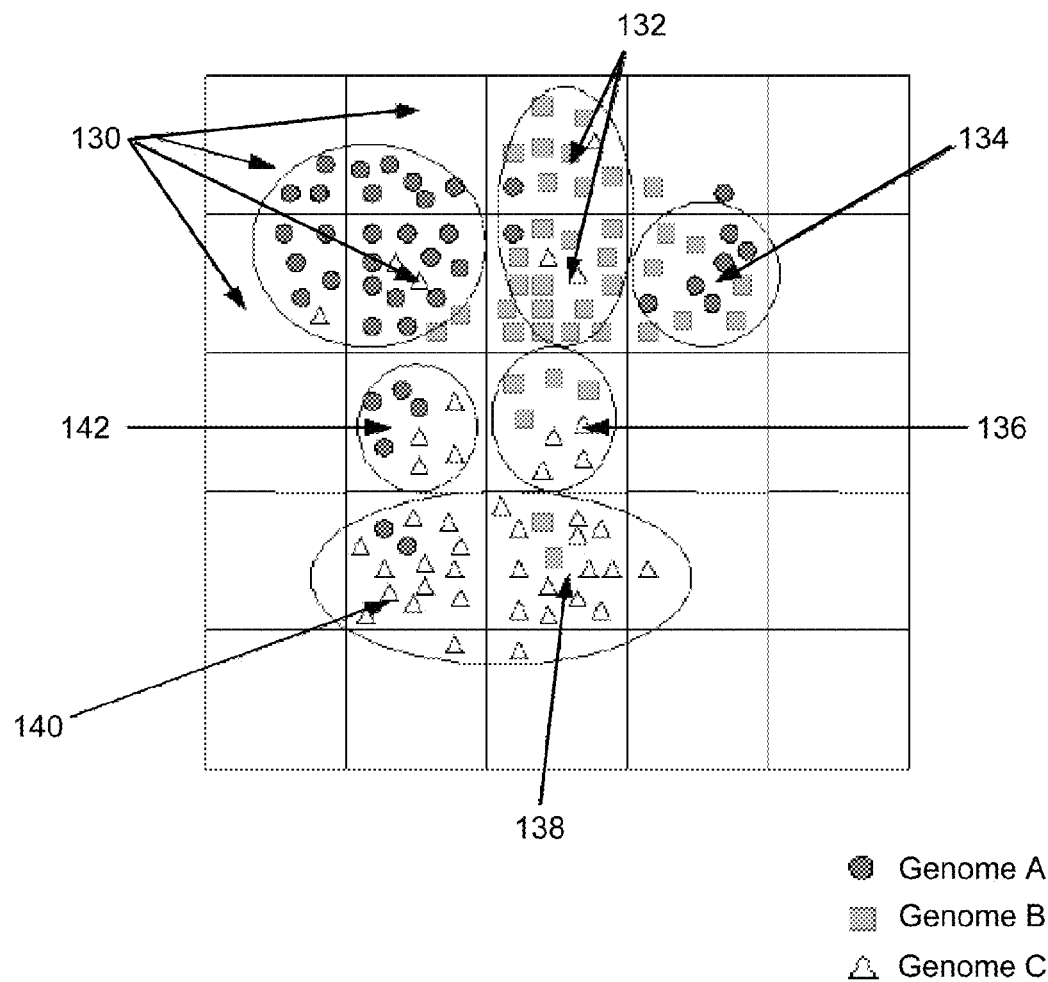
FIG. 1(b) illustrates a grid framework showing a pattern of localization of fragment points corresponding to the genomic fragments, in accordance with an embodiment of the present subject matter.

For example in FIG. 1(b), a grid framework showing pattern of localization of the fragment points corresponding to the genomic fragments originating from three different genomes A, B, and C is shown. These fragment points, circular, square, and triangular in shape, in the given grid framework represent genomes A, B, and C respectively. Reference numeral 130 indicates the majority grids of genome A and minority grids of genome C. The majority grids of genome B and minority grids of genome C are represented by arrows of reference numeral 132. Similarly, reference numerals 134, 136, 138, 140, and 142 represent mixed grids of genomes A and B, mixed grids of genomes B and C, majority grids of genome C and minority grids of genome B, majority grids of genome C and minority grids of genome A, and mixed grids of genomes A and C respectively.

In one implementation, a quantile function value approach is used to identify a percentile value to efficiently identify each grid as one of majority, minority, and mixed grids with the help of equations (3) and (4). For example, percentile value (τ) may be chosen as 0.25, i.e., as the quartile value, by performing various validation tests with different quantile function values.

$$Q(\tau)=F^{-1}u, u \in [0,1] \quad (3)$$

$$F^{-1}(u)=\inf\{F(x)\geq u\}, x \in R \quad (4)$$

Where, $Q(\tau)$=Quantile function for percentile (τ) and $F^{-1}(u)$=Inverse of cumulative distribution function.

The HGT prediction module 114 determines the quartile values corresponding to the percentile value obtained. In continuation with the last example, quartile values 0.25, 0.50, 0.75, and 1 may be Obtained corresponding to 0.25 percentile value. The obtained quartile values are referred to as Q1, Q2, Q3, and Q4. Subsequently, the HGT prediction module 114 determines a threshold for classifying each grid as one of majority, minority, and mixed grids. In one implementation, equation (5), (6), and (7) may be used for determining the thresholds, referred to as $R_G$ and $R_L$.

$$R_G=Q3+\text{IQD}*n \quad (5)$$

$$R_L=Q3-\text{IQD}*n \quad (6)$$

$$\text{IQD}=Q3-Q1 \quad (7)$$

Where, IQD is an inter-quartile distance and n is a genome-specific value.

The genome-specific value 'n' depends upon genome size and its grid occupancy pattern. The genome-specific value can be determined by extensive validation on various genomes belonging to the genomes 126. For example, the HGT prediction module 114 performs a validation test on 50 genomes of varying sizes (from the smallest to the largest genome size) which were observed to have different grid occupancy patterns. To ascertain the correct value(s) of parameter 'n' and for efficient inter-genome comparisons of genomes of varying sizes, the HGT prediction module 114 obtains a ratio $R_n$ using a series of parametric tests. For any given genome, the $R_n$ represents the ratio of its genome size to the total number of grids occupied by the fragment points belonging to that genome. Finally, based on these parametric tests on various different genomes, the HGT prediction module 114 determines the genome-specific value using a step-algorithm technique for different ranges of the ratio $R_n$.

In one implementation, the HGT prediction module 114 may categorize the genomes into a plurality of categories based on the range of values obtained for the ratio $R_n$. For example, a first category may include genomes of large sizes containing extremely high compositionally distinct regions. Consequently, fragment points belonging to these genomes would be localized to a very large number of grids due to the presence of a extremely large number of compositionally distinct regions. In one implementation, the value of ratio $R_n$ varies from 0 to 3 for the genomes of the first category and the HGT prediction module 114 sets the genome-specific value, i.e., 'n' as 2.5. Similarly, a second category may include genomes of intermediate to large sizes having high number of compositionally distinct regions. Fragment points belonging to the genomes of this category are localized in a large number of grids, which are lower than those observed for genomes belonging to the first category. In one implementation, the value of ratio $R_n$, varies from 3 to 6 for the genomes of the second category and the HGT prediction module 114 sets the genome-specific value 'n' as 2.0. Further, a third category may include genomes of small to large sizes, having relatively fewer compositionally distinct regions, as compared to the genomes belonging to the first two categories. As a result, the fragment points belonging to the genomes of this category are localized to a relatively fewer number of grids as compared to those of the genomes belonging to the first two categories. In one implementation, the value of ratio $R_n$ varies from 6 to 9 for the genomes of the third category and the HGT prediction module 114 sets the genome-specific value 'n' as 1.5.

A fourth category may include genomes of varying sizes, from small to large, and having less compositionally distinct regions. Consequently, the fragment points belonging to such genomes are localized in a relatively lesser number of grids as compared to the genomes belonging to the first three categories. In one implementation, the value of ratio $R_n$ varies from 9-12 for the genomes of the fourth category and the HGT prediction module 114 sets the genome-specific value 'n' as 1.0. Similarly, a fifth category may include genomes of very small to intermediate sizes, and containing very few compositionally distinct regions. As a result, the fragment points corresponding to such genomes are observed to be localized in very few grids as compared to all other categories of genomes described above. In one implementation, the value of ratio $R_n$ is always greater than 12 for the genomes of the fifth category and the HGT prediction module 114 sets the genome-specific value 'n' as 0.5. Thus, by including the genome-specific value along with inter-quartile distance for determination of the threshold values, the effect of genome size and grid occupancy pattern is normalized.

For a given grid, the HGT prediction module 114 may use the threshold values computed as explained above to classify the grid as follows. If the number of fragment points of the selected genome in the given grid is greater than or equal to $R_G$, the given grid is classified as majority grid for the selected genome. If the number of fragment points of the selected genome in the given grid is less than $R_G$, but greater than $R_L$, the given grid is classified as mixed grid for the selected genome. If the number of fragment points of the selected genome in the given grid is less than $R_L$, the given grid is classified as minority grid for the selected genome.

Figure 1C:
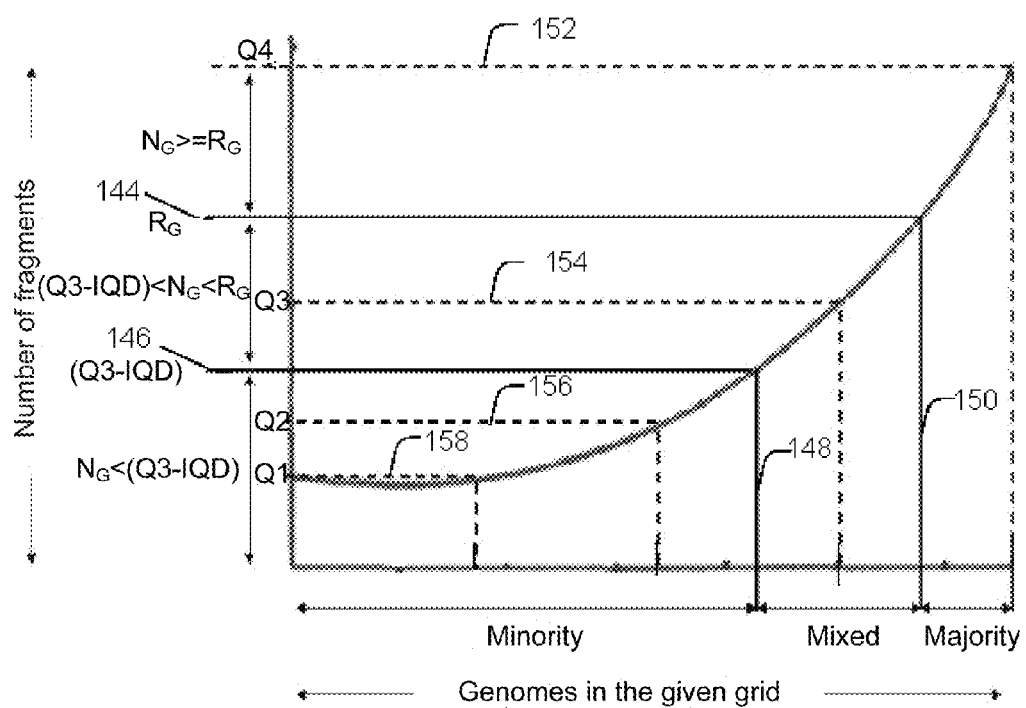
FIG. 1(c) illustrates a graph depicting classification of grids as majority, minority, and mixed grids based on thresholds and number of fragments, in accordance with an embodiment of the present subject matter.

For example, in FIG. 1(c), a plot of the number of fragment points for the different genomes in a given grid is shown. The vertical axis in the plot represents the number of fragment points corresponding to the genomic fragments for each of the genomes and horizontal axis represents the genomes in the given grid. The lines intersecting the vertical axis represented by reference numerals 144 and 146 depict the threshold values $R_G$ and $R_L$. The thresholds divide the plot in three regions. These three regions are classified as majority, minority, and mixed grids and are used to demarcate the genomes on the x-axis accordingly. The reference numerals 152, 154, 156, and 158 represent the different quartile values Q4, Q3, Q2, and Q1 respectively. Based on these quartile values the thresholds $R_G$ and $R_L$ may be calculated. The genomes falling before intersection on the horizontal axis represented by reference numeral 148 are in minority, genomes falling between line of intersection on horizontal axis represented by reference numerals 148 and 150 are neither in minority nor in majority, referred to as mixed, and genomes falling beyond the line of intersection on the horizontal axis represented by reference numeral 150 on the plot are in majority in the given grid.

Further, the HGT prediction module 114 selects only the mixed and minority grids corresponding to the selected genome for detection of HGT in the selected genome. Those genomic fragments of the selected genome are identified to be probable HGT regions for which the corresponding fragment points lie within a certain threshold distance from the centroid corresponding to the home grid. A grid, in which the fragment point corresponding to the genomic fragment lies, is referred to as home grid. Grids immediately attached to the home grid are referred to as neighboring grids.

In one implementation, the HGT prediction module 114 uses a distance ratio assessment to identify the probable HGT. For this, the HGT prediction module 114 computes the ratios of distance of a given fragment point from the centroid of the home grid to distance between the centroid of the home grid and centroids of the neighboring grids. Separate distance ratios are calculated with respect to each neighboring grid. For example, equation (8) may be used for calculating the distance ratio (R).

$$R = D_{HP}/D_{HJ} \qquad (8)$$

Where, $D_{HP}$ is the distance between fragment point of genomic fragment P to centroid of home grid H and $D_{HJ}$ is the distance between centroid of home grid H to centroid of neighboring grid J.

For a given fragment, if the distance ratios obtained with respect to all neighboring grids are less than a distance threshold, say 0.5, the HGT prediction module 114 considers it as a probable HGT fragment, also referred to as predicted HGT fragment. If, for a given fragment, the ratio obtained with respect to even one of the neighboring grids is observed to be more than the distance threshold, the fragment is attached to that neighboring grid. In case, one or more distance ratios are observed to be greater than the distance threshold, the fragment is attached to the nearest neighboring grid having a distance ratio more than the distance threshold. Each of the minority and mixed grids of the selected genome are thus analyzed to determine the probable HGT fragments. Finally, the HGT prediction module 114 stores the predicted HGT in the HGT data 120.

In one implementation, the HGT prediction module 114 associates a confidence value to each predicted HGT using a distance based score. Once, the set of probable HGT fragments are determined, confidence scores are further awarded to each of these predicted HGT fragments based on their extent of closeness to the given minority or mixed grid. In one implementation, the HGT prediction module 114 obtains a projection of the centroid of a grid and all the fragment points located in that grid on each of the three x-y, x-z, and y-z planes. The distances are calculated between the projection of the centroid on a particular plane and each of the constituting fragment points corresponding to the genomic fragments. The maximum distance on the plane is referred to as Dmax. Further, the HGT prediction module 114 draws three concentric circles with radii Dmax, 2Dmax/3, and Dmax/3 with the projected centroid on the plane as center. The three circles divide the plane into three concentric regions. Finally, the HGT prediction module 114 computes a confidence value based on the position of the projected fragment point corresponding to the given genomic fragment predicted as HGT in each plane. The confidence values obtained for each of the three planes are added to obtain a cumulative confidence value. The genomic fragments predicted as HGT, having a higher confidence score has a higher probability of being a true HGT.

Figure 1D:
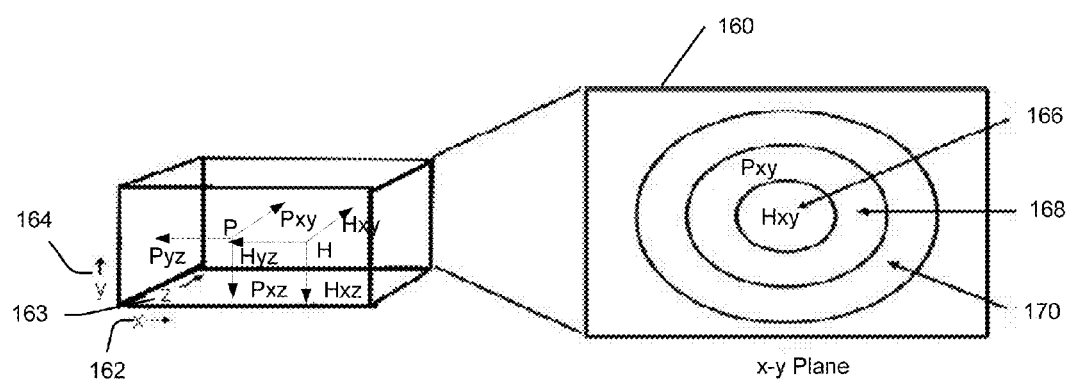
FIG. 1(d) illustrates a pictorial representation of method for associating a confidence score based on the location of fragment point, in accordance with an embodiment of the present subject matter.

For example in FIG. 1(d), the three concentric regions are generated on the x-y plane 160 for a given grid. The given grid has the x axis 162 along the horizontal axis and y axis 164 along the vertical axis and has the z-axis 163 pointing perpendicular to the x-y plane 160. The confidence value is associated with the three projections of the point predicted as probable HGT. The centroid of the given grid is taken as center of the concentric circles. For each of the x-y, y-z and x-z planes, a confidence value of 3 may be associated to the probable HGT. If the point lies in the innermost region 166. For the region 168 in between the outer most region 170 and inner most region 166, a confidence value of 2 is associated with the probable HGT. If the point of probable HGT lies in the outermost region 170, a confidence value of 1 is assigned. Similarly, the confidence values for other planes can be calculated, Finally, the HGT prediction module 114 obtains a cumulative confidence value by adding the confidence values corresponding to each of the x-y, y-z, and x-z planes. The predicted HGT having higher cumulative confidence value has a higher probability of being a true HGT and vice versa. The cumulative confidence value may be further rank-normalized to a value between 0 and 10 for better comparison across genes and genomes.

VALIDATION AND RESULTS

The results of the present horizontally transferred gene prediction method have been validated using five simulated microbial genomes originating from *Archaeoglobus fulgidus, Methanococcus jannoschii, Neisseria gonorrhoeae, Ralstonia solanacearum*, and *Sinorhizobium meliloti*. These simulated genomes have been used in conventional systems to benchmark and compare various parametric HGT prediction approaches. Each of these five simulated genomes has genomic regions, inserted from the other four simulated genomes in proportions so as to mimic real HGT events.

These artificial horizontally transferred genomic regions are generally expected to be predicted as HGT regions by an HGT prediction system, such as the HGT prediction system 100. The results of HGT prediction obtained using the HGT Prediction System 100 were compared with the results obtained with two conventionally known techniques, viz., Alien Hunter (IVOM), and Wn (Chi) techniques. Further, efficiency of different HGT prediction systems were evaluated using two factors, namely, sensitivity and false positive rate. The sensitivity, also referred to as SS, and false-positive rate, also referred to as FPR, of the present subject matter were compared with Alien Hunter and Wn techniques for all the five simulated microbial genomes. The sensitivity and false positive rate values achieved by all three methods for each of the five simulated microbial genomes have been provided in Table 1.

TABLE 1

| Genome | Current Approach | | Alien Hunter (IVOM) | | Wn (Chi) | |
|---|---|---|---|---|---|---|
| | SS | FPR | SS | FPR | SS | FPR |
| A. fulgidus | 88.29 | 9.89 | 96.59 | 8.71 | 90.73 | 8.05 |
| M. jannaschii | 94 | 11.66 | 86 | 3.9 | 85.33 | 4.86 |
| N. gonorrhoeae | 83.64 | 20.98 | 86.36 | 9.43 | 75 | 7.52 |
| R. solanacearum | 81.02 | 15.78 | 76.2 | 4.62 | 73.94 | 4.27 |
| S. meliloti | 84.71 | 10.83 | 76.45 | 5.23 | 74.92 | 3.96 |
| Mean | 86.33 | 13.83 | 84.32 | 6.38 | 79.98 | 5.73 |
| Std Dev | 5.02 | 4.59 | 8.45 | 2.52 | 7.60 | 1.91 |

It can be gathered from table 1 that sensitivity values obtained with the current HGT prediction technique are higher than Alien Hunter and Qn (Chi) technique in three and four out of five simulated microbial genomes respectively. Further, it can be seen that the present HGT technique has higher mean sensitivity value as compared to the other two techniques.

Additionally, the false positive rates of the current HGT prediction technique are also acceptably low and are only marginally higher than that obtained using the other two techniques. As would be known to a person skilled in the art, if the other two methods try to achieve similar sensitivity as obtained by the HGT prediction system 100, their false positive rates is likely to be higher or equivalent in comparison to false positive rates of HGT prediction system 100. The results indicate the HGT prediction system 100 may be used for the efficient detection of the HGT regions in genomes originating from diverse taxonomic clades.

Figure 2:
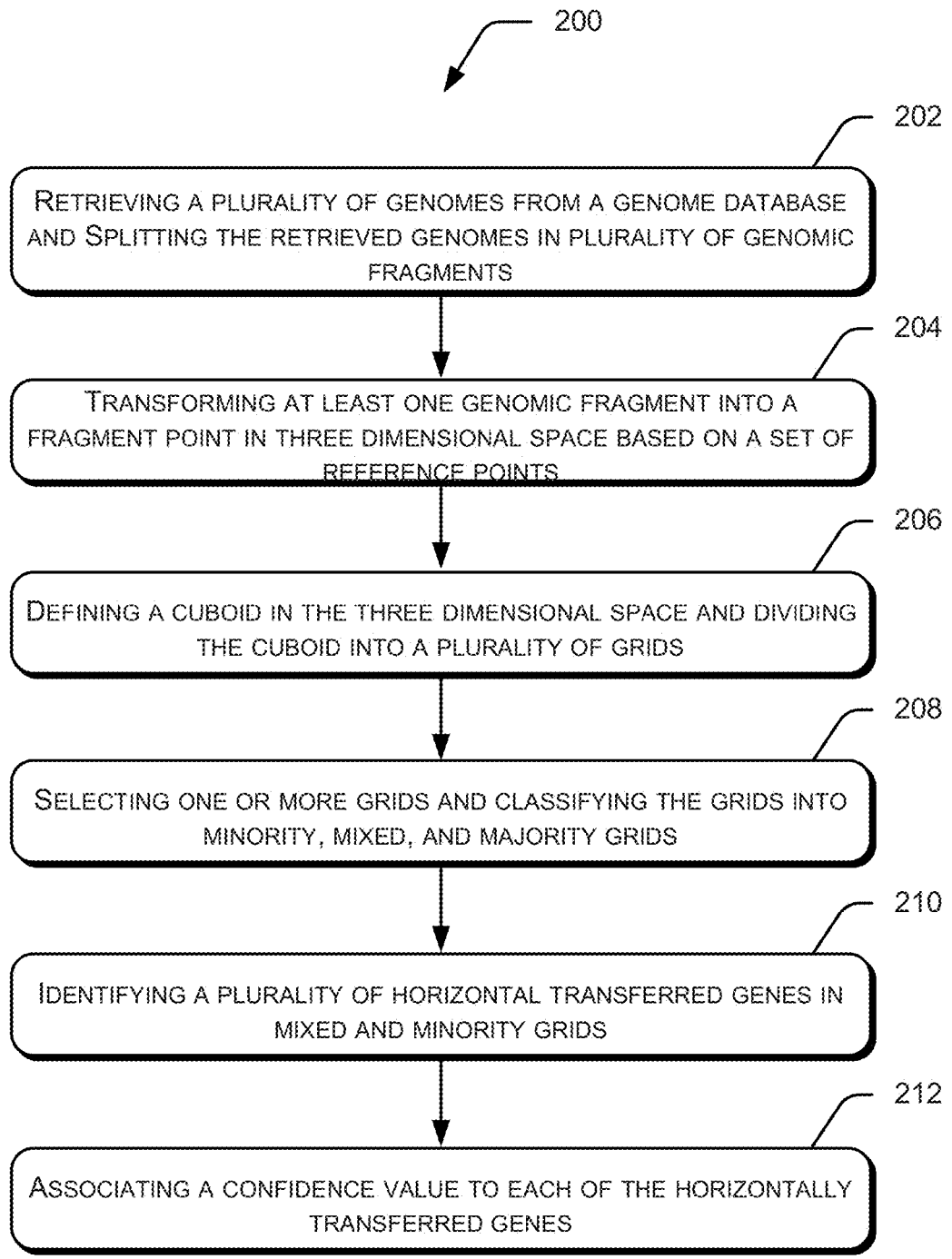
FIG. 2 illustrates an exemplary method for prediction of horizontally transferred gene, in accordance with an implementation of the present subject matter.
Figure 3:
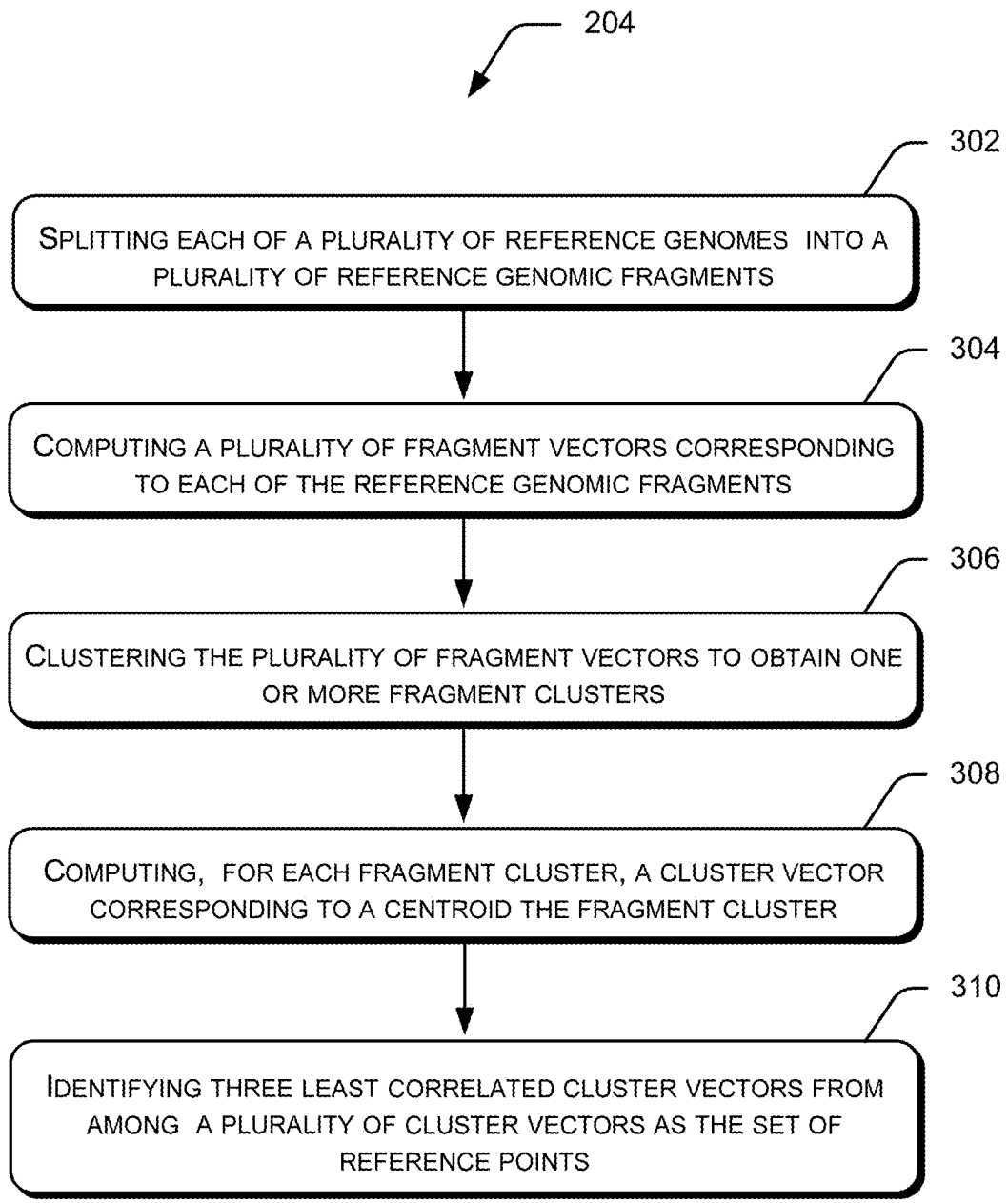
FIG. 3 illustrates an exemplary method to transform a genomic fragment into a fragment point in a three dimensional space, in accordance with an implementation of the present subject matter.
Figure 4:
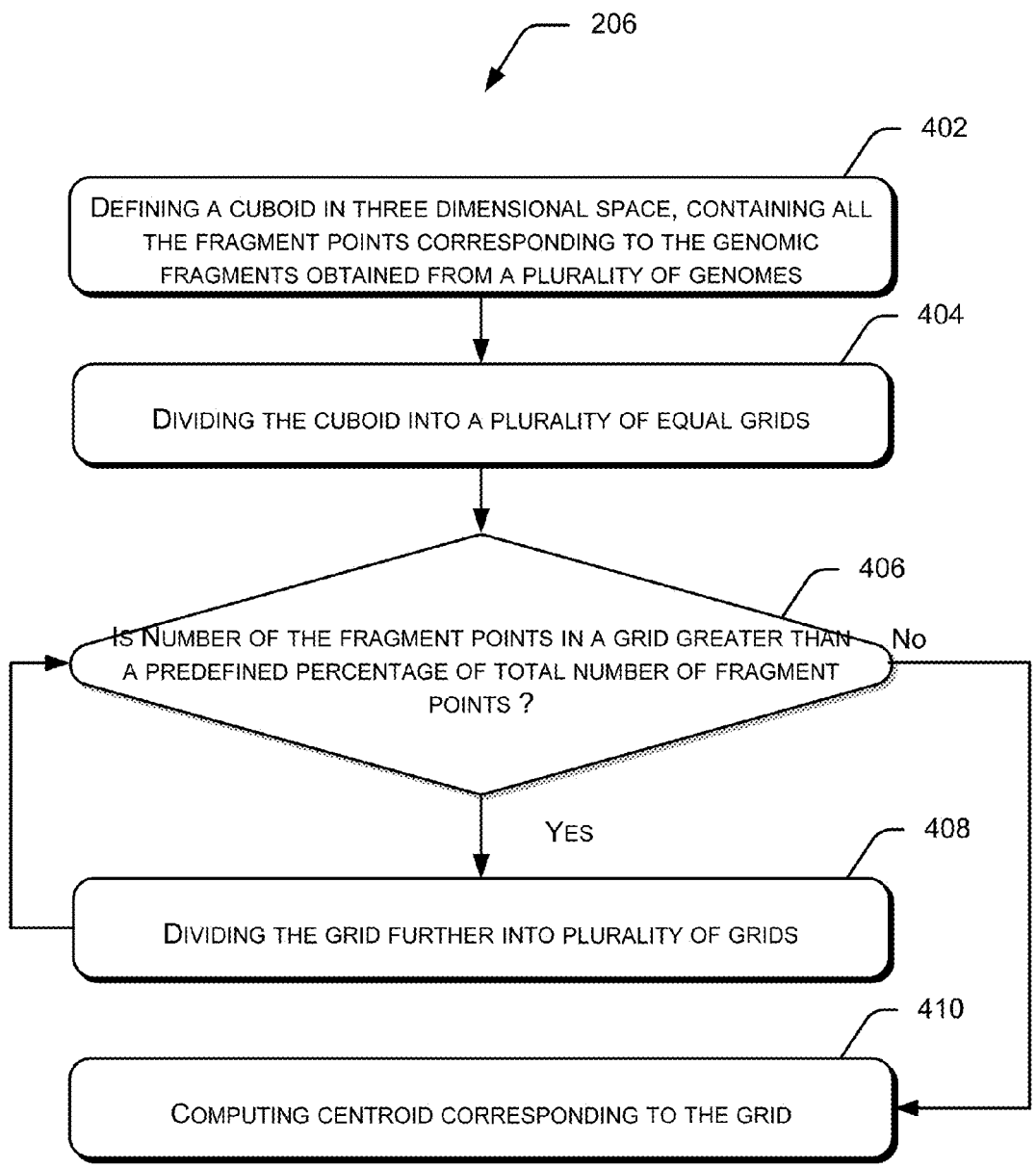
FIG. 4 illustrates an exemplary method to define a cuboid having grids and including fragment points corresponding to genomic fragments in a three dimensional space, in accordance with an implementation of the present subject matter.
Figure 5:
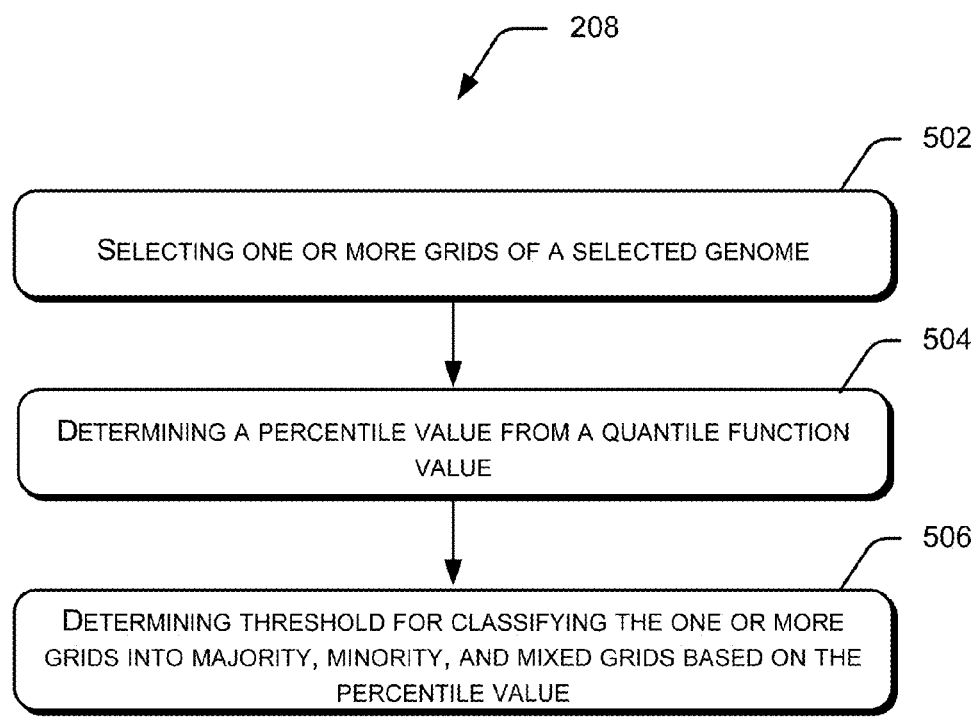
FIG. 5 illustrates an exemplary method to classify selected grids as one of minority, majority, and mixed grids, in accordance with an implementation of the present subject matter.

FIG. 2 illustrates a method 200 for predicting HGT, FIG. 3 illustrates a method to transform a genomic fragment into a fragment point in a three dimensional space, FIG. 4 illustrates a method to define a cuboid to enclose the fragment points corresponding to all the genomic fragments in the three dimensional space, and FIG. 5 illustrates a method to classify selected grids as one of minority, majority, and mixed grids, in accordance with an implementation of the present subject matter.

The exemplary methods may be described in the general context of computer executable instructions. Generally, computer executable instructions can include routines, programs, objects, components, data structures, procedures, modules, functions, etc., that perform particular functions or implement particular abstract data types. The methods may also be practiced in a distributed computing environment where functions are performed by remote processing devices that are linked through a communications network. In a distributed computing environment, computer executable instructions may be located in both local and remote computer storage media, including memory storage devices.

The order in which the methods are described is not intended to be construed as a limitation, and some of the described method blocks can be combined in any order to implement the method, or an alternative method. Additionally, individual blocks may be deleted from the methods without departing from the spirit and scope of the subject matter described herein. Furthermore, the methods can be implemented in any suitable hardware, software, firmware, or combination thereof.

At block 202, a plurality of genomes from a database of genomes, such as the genomic database 124 is retrieved by, for example, the transformation module 112. Further, the plurality of genomes 126 is split into a plurality of genomic fragments. In an example, the genomic fragments are stored in the transformation data 118.

At block 204, the genomic fragments are transformed into fragment points in a three dimensional space by, for example, the transformation module 112. In an example, the transformation may be carried out using a set of reference points. The transformation of genomic fragments will be explained in detail with reference to description of FIG. 3.

At block 206, a cuboid is defined to enclose all the genomic fragments in the three dimensional space based on the set of reference points. In one implementation, the transformation module 112 is configured to define the cuboid. The cuboid is further divided into a plurality of equally sized smaller cuboids called grids, in case of dense grids, i.e., grids in which the number of genomic fragments is greater than a threshold proportion of total number of genomic fragments, the dense grids are further resolved into smaller grids. The details pertaining to defining the cuboid and the grids in the three dimensional space will be explained in detail with reference to description of FIG. 4.

At block 208, one or more grids are selected from the plurality of grids, by for example, the HGT prediction module 114. The grids include the genomic fragments of a selected genome. The selected genome from the plurality of genomes 126 is the genome under the consideration for prediction of probable HGT regions. The selected grids are then classified as at least one of majority, minority, and mixed grids. The basis of classification will be explained in detail with reference to description of FIG. 5.

At block 210, probable horizontally transferred genes or cluster of genes are identified in the minority and mixed grids. The identified HGT are stored in the HGT data 120. Since compositionally distinct or horizontally transferred regions of a given genome are expected to be localized to certain grids, where the abundance of the genomic fragments originating from the given genome is low, only the mixed and minority grids corresponding to the given genome may be analyzed for HGT prediction.

The grid containing the genomic fragment under consideration for detection of probable HGT is referred to as a home grid. The immediate neighbors of the home grid are referred to as neighboring grids. The ratio of distance of a fragment point corresponding to a given genomic fragment from the centroid of the home grid to distance of centroid of the home grid from centroid of a neighboring grid is computed. This ratio of distance is computed with respect to each neighboring grid. If, for each neighboring grid, the ratio is below a threshold, for example 0.5, then the genomic fragment is identified as HGT. However, if the ratio is above or equal to the threshold for at least one neighboring grid, the corresponding fragment point is attached to the nearest neighboring grid.

At block 212, a confidence value is associated to each predicted HGT by, for example the HGT prediction module 114. The projections of centroid of the grid and fragment points corresponding to the genomic fragments belonging to that grid are obtained on each of the x-y, x-z, and y-z planes. For each plane, a distance is computed between the projection of the centroid of that grid on the plane and the projections of each of the constituting fragment points corresponding to the genomic fragments. The maximum distance obtained is referred to as Dmax. Further, three concentric circles with radii Dmax, 2*Dmax/3 and Dmax/3 are obtained on the plane with projection of centroid of the grid as the center. The three circles with the given radii divide each of the planes into three concentric regions. The confidence value is associated to the fragment point corresponding to the predicted HGT, based on the region in which its projection falls. In one implementation, if the projection of the fragment point falls within the innermost concentric region, a confidence value of 3 is awarded. If the projection of the fragment point lies between the first and the second concentric circle, a confidence value of 2 is awarded. If the projected fragment point lies between the second and the third circle, a confidence value of 1 is awarded. Finally, the confidence values obtained for this point in each of the x-y, x-z and y-z planes are summed to obtain a cumulative confidence value by the HGT prediction module 114. The predicted HGT having higher confidence value has a higher probability of being a true HGT and vice versa. The predicted HGT along with the associated confidence value is stored in the HGT data 120. In one implementation, in order to enable an efficient inter-grid comparison of all predicted HGT fragments, the confidence values may be rank-normalized between 0 and 10.

Referring to FIG. 3 that illustrates details of the method 204 for transforming a genomic fragment into a point in three dimensional space, according to an implementation of the present subject matter. The transformation is carried out with the help of a set of reference points obtained from a plurality of reference genomes 128.

At block 302, a plurality of reference genomes 1128 is retrieved from a genome database 124. Each of the reference genomes is representative of one genus. The plurality of reference genomes 128 thus retrieved is split into a plurality of non-overlapping reference genomic fragments. For example, 237 completely sequenced microbial genomes may be retrieved from the reference genomes 128 and split into 1000 base pair non-overlapping reference genomic fragments.

At block 304, a plurality of fragment vectors corresponding to each of the non overlapping reference genomic fragments is computed and stored in the transformation data 118. In one implementation, the computing and storing is performed by the transformation module 112. In one implementation, the fragment vectors are 256 dimensional vectors representing the frequencies of the 256 possible tetra nucleotides in the respective fragments.

At block 306, the plurality of fragment vectors obtained is clustered by using clustering approaches. In one implementation, the K-means approach may be used by the transformation module 112 for clustering of the plurality of fragment vectors.

At block 308, cluster vectors corresponding to the centroids of each of the clusters are computed by, for example, the transformation module 112. The computed cluster vectors are stored in the transformation data 118. The cluster vectors are further used for identifying the set of reference points.

At block 310, the set of reference points is obtained by computing pairwise dot products between the unit cluster vectors. The three cluster vectors having the least pairwise dot products amongst them are taken as the set of reference points by the transformation module 112. This set of reference points are used to map the fragment points corresponding to the genomic fragments belonging to genomes 126 in order to generate the first cuboid as discussed earlier. The next three cluster vectors (i.e. $4^{th}$, $5^{th}$, $6^{th}$) having the least pairwise dot products amongst them are taken as new set of reference points for further dividing the dense grids into smaller grids as discussed earlier.

Referring to FIG. 4 that illustrates details of the method 206 to define a cuboid to enclose all the fragment points corresponding to the genomic fragments of the genomes 126 in the three dimensional space and dividing the cuboid into a plurality of grids, in accordance with one implementation of the present subject matter.

At block 402, a cuboid is defined in a three dimensional space by, for example, the transformation module 112. The ranges of the x, y, and z dimensions of the cuboid are computed as the difference of the maximum and minimum values for the x, y, and z coordinates of the fragment points. Thus, the cuboid includes all the fragment points corresponding to the genomic fragments from the genomes 126.

At block 404, the cuboid is divided into a plurality of smaller cuboids called grids. In one implementation the size of the grids may be equal to each other. For example, the cuboid defined in the three dimensional space may be divided into 1000 equal grids. The fragment points corresponding to the genomic fragments falling in the same grid are grouped together.

At block 406, it is determined if a grid is a dense grid, i.e., if the number of the fragment points for a given grid is equal to or more than a predefined percentage of the total number of the fragment points. For example, the transformation module 112 determines if the number of the fragment points for a given grid is equal to or more than five percent of the total number of the fragment points. In case of dense grids, block 408 is executed. Else, block 410 is executed.

At block 408, the given grid is further divided into smaller grids by the transformation module 112. This block may be repeated unless the number of fragment points in the dense grids becomes less than five percent of total number of the genomic fragments. In one implementation, dividing the dense grids two times may be sufficient to obtain a set of grids, where in none of the grids can be further classified as a dense grid. The division of dense grid into smaller grids is done with the help of a new set of reference points, obtained in the block 310 of FIG. 3.

At block 410, once all the dense grids are divided into smaller grids and no more grids are left to be classified as dense grids, a centroid corresponding to each grid is computed and stored in the transformation data 118 for future use in identifying the probable HGT.

Referring to FIG. 5 that illustrates details of the method 208 for classifying the grids as one of majority, minority, and mixed grids, in accordance with one embodiment of the present subject matter. Different approaches may be used to classify grids. In one implementation quantile function value approach is used to classify the grids as at least one of majority, minority, and mixed grids.

At block 502, one or more grids are selected for a selected genome by the HGT prediction module 114. The selected genome is the genome under consideration for determining an HGT in that genome. The one or more grids include all the fragment points corresponding to the genomic fragments of the selected genome.

At block 504, the HGT prediction module 114 identifies, for classifying the grids, a percentile value which is obtained using a set of different quantile function values. In one implementation, nature of the grid population may be determined for classification. Subsequently, validation tests may be performed with various quantile function values to determine a percentile value that would be efficient in classifying the one or more selected grids. For example, a percentile value of 0.25 may be found to be efficient for classifying the grids.

At block 506, different quartile values corresponding to the percentile values of 0.25, 0.5, 0.75 and 1.0 are determined by the HGT prediction module 114. The different quartile values are referred to as Q1, Q2, Q3, and Q4. Based on the different quartile values, a threshold for classifying the grids as one of majority, minority, and mixed grids is determined for the selected genome. The threshold value obtained depends on certain parameters, such as genome size and grid occupancy pattern.

CONCLUSION

Although embodiments for HGT prediction have been described in language specific to structural features and/or methods, it is to be understood that the invention is not necessarily limited to the specific features or methods described. Rather, the specific features and methods are disclosed as exemplary embodiments for method and system for HGT prediction.

We claim:

1. A computerized method for identifying a horizontally transferred gene, the method comprising:
    sequencing genetic material obtained from a plurality of organisms to obtain a plurality of sequenced microbial genomes;
    computing pairwise dot products between unit cluster vectors determined from a plurality of reference genomes;
    selecting three most orthogonal cluster vectors as a set of reference points, based on the computed pairwise dot products, wherein the three selected cluster vectors have least pairwise dot product amongst their respective unit cluster vectors;
    transforming genomic fragments, from the plurality of sequenced microbial genomes, into fragment points based on the set of reference points;
    defining a cuboid in a three dimensional space, wherein the cuboid encompasses the fragment points corresponding to the genomic fragments from the plurality of sequenced microbial genomes;
    dividing the cuboid iteratively into a plurality of grids, wherein a number of fragment points corresponding to the genomic fragments in each grid is less than a predefined percentage of total number of genomic fragments;
    selecting one or more grids corresponding to a selected genome from the plurality of grids;
    classifying each of the selected grids as one of majority, minority, and mixed grids, based on a threshold defining a minimum number of fragment points corresponding to the selected genome in a grid, for the grid to be classified as a majority grid for the selected genome, and another threshold defining a maximum number of fragment points corresponding to the selected genome in the grids, for the grid to be classified as a minority grid; and
    identifying, from the minority and the mixed grids, at least one compositionally distinct genomic fragment corresponding to the horizontally transferred gene as a horizontally transferred gene fragment based on a distance ratio assessment.

2. The method as claimed in claim 1, wherein the dividing comprises dividing a dense grid in the plurality of grids into a plurality of smaller grids using a second set of reference points, wherein number of fragment points in the dense grid is more than a predefined percentage of total number of the genomic fragments.

3. The method as claimed in claim 1, wherein the classifying further comprises:
    determining a plurality of quartile values corresponding to a selected percentile value, wherein the quartile values correspond to distribution of number of fragments of each of the genomes in each of the plurality of grids in the cuboid;
    computing genome specific value, based on a number of grids occupied by the fragment points belonging to the selected genome and a size of the selected genome; and
    computing thresholds for classifying the one or more selected grids as one of the majority, the minority, and the mixed grids, based on the plurality of quartile values and the genome-specific value.

4. The method as claimed in claim 1, wherein the distance ratio assessment includes computing, for each neighboring grid, a ratio of distance of a fragment point from a centroid of a home grid to distance of the centroid of the home grid from a centroid of the neighboring grid.

5. The method as claimed in claim 1, wherein each fragment point corresponding to a genomic fragment having a distance ratio for each neighboring grid below a predefined value is identified as belonging to the horizontally transferred gene.

6. The method as claimed in claim 1 further comprises:
    obtaining a projection of a centroid of a home grid in each of a plurality of two dimensional planes;
    obtaining a projection of each of the fragment points in the home grid in each of a plurality of two dimensional planes; and
    associating, for each of the plurality of two dimensional planes, a confidence value to the identified horizontally transferred gene fragment, wherein the confidence value is obtained by computing a distance between the projection of each of the fragment points in a two dimensional plane and the projection of the centroid in the dimensional plane.

7. The method as claimed in claim 6, wherein the method further comprises adding the confidence values for the plurality of two dimensional planes to obtain a cumulative confidence value for the identified horizontally transferred gene fragment, wherein the cumulative confidence value is rank normalized across all fragment points in the home grid to obtain a rank-normalized confidence value.

8. A horizontally transferred gene (HGT) prediction system comprising:
    a processor; and
    a memory coupled to the processor, the memory comprising:
    a module configured to create a plurality of sequenced microbial genomes by sequencing genetic material extracted from a plurality of organisms;
    a transformation module configured to,
        obtain a plurality of sequenced microbial genomes from a genome database, the genome database including genomic sequences corresponding to a plurality of sequenced microbial genomes, wherein each of the genomic sequences is created by sequencing genetic material extracted from a plurality of organisms;
        compute pairwise dot products between unit cluster vectors determined from a plurality of reference genomes;
        select three most orthogonal cluster vectors as a set of reference points, based on the computed pairwise dot products, wherein the three selected cluster vectors have least pairwise dot product amongst their respective unit cluster vectors;

transform genomic fragments, from the plurality of sequenced microbial genomes, into fragment points in a three dimensional space based on the set of reference points;

define a cuboid including the fragment points; and divide the cuboid iteratively into grids, wherein a number of fragment points corresponding to the genomic fragments in each grid is less than a predefined percentage of total number of genomic fragments; and an HGT prediction module configured to, classify each of a plurality of selected grids corresponding to a selected genome as one of minority, majority, and mixed grids, based on a threshold defining a minimum number of fragment points corresponding to the selected genome in a grid, for the grid to be classified as a majority grid for the selected genome, and another threshold defining a maximum number of fragment points corresponding to the selected genome in the grids, for the grid to be classified as a minority grid;

identify one or more horizontally transferred gene fragments in the minority and the mixed grids; and associate a confidence value to each of the horizontally transferred gene fragments.

9. The HGT prediction system as claimed in claim 8, wherein the HGT prediction module is further configured to compute a distance ratio for each neighboring grid, wherein the distance ratio corresponds to a ratio of distance of a fragment point from a centroid of a home grid to distance of the centroid of the home grid from a centroid of the neighboring grid.

10. The HGT prediction system as claimed in claim 8, wherein the transformation module is further configured to identify a dense grid in which number of genomic fragments is more than the predefined percentage of the total number of the genomic fragments.

11. The HGT prediction system as claimed in claim 8, wherein the transformation module is further configured to divide the dense grid amongst the plurality of grids into a plurality of smaller grids using a second set of reference points.

12. The HGT prediction system as claimed in claim 8, wherein the HGT prediction module is further configured to:

determine a plurality of quartile values corresponding to a selected percentile value, wherein the quartile values correspond to distribution of number of fragments of each of the genomes in each of the plurality of grids in the cuboid;

compute genome specific value, based on a number of grids occupied by the fragment points belonging to the selected genome and a size of the selected genome; and compute thresholds for classifying the selected grids as one of majority, minority, and mixed grids, based on the plurality of quartile values and the genome-specific value.

13. The HGT prediction system as claimed in claim 8, wherein the HGT prediction module is further configured to identify the genomic fragments having a distance ratio for each neighboring grid below a predefined value as the horizontally transferred gene fragments.

14. HGT prediction system as claimed in claim 8, wherein the HGT prediction module is configured to:

obtain a projection of a centroid of a home grid in each of a plurality of two dimensional planes;

obtain a projection of each of the fragment points in the home grid in each of the plurality of two dimensional planes; and obtain the confidence value by computing a distance between the projection of each of the fragment points in a two dimensional plane and the projection of the centroids in the two dimensional plane.

15. The HGT prediction system as claimed in claim 14, wherein the HGT prediction module is configured to add the confidence values obtained for the plurality of two dimensional planes, associated with each of the identified horizontally transferred gene fragments to obtain a cumulative confidence value for the identified horizontally transferred gene fragment, wherein the cumulative confidence value is rank normalized across all fragment points in the home grid to obtain a rank-normalized confidence value.

16. A non-transitory computer readable medium having embodied thereon a computer program for executing a method comprising;

sequencing genetic material obtained from a plurality of organisms to obtain a plurality of sequenced microbial genomes;

computing pairwise dot products between unit cluster vectors determined from a plurality of reference genomes;

selecting three most orthogonal cluster vectors as a set of reference points, based on the computed pairwise dot products, wherein the three selected cluster vectors have least pairwise dot product amongst their respective unit cluster vectors;

transforming genomic fragments, from the plurality of sequenced microbial genomes, into fragment points based on the set of reference points;

defining a cuboid in a three dimensional space, wherein the cuboid includes the fragment points corresponding to the genomic fragments;

dividing the cuboid iteratively into a plurality of grids, wherein a number of fragment points corresponding to the genomic fragments in each grid is less than a predefined percentage of total number of genomic fragments;

selecting one or more grids corresponding to a selected genome;

classifying each of the selected grids as one of majority, minority, and mixed grids, based on a threshold defining a minimum number of fragment points corresponding to the selected genome in a grid, for the grid to be classified as a majority grid for the selected genome, and another threshold defining a maximum number of fragment points corresponding to the selected genome in the grids, for the grid to be classified as a minority grid; and identifying, from the minority and the mixed grids, at least one fragment point as the horizontally transferred gene fragment based on a distance ratio assessment.

* * * * *